United States Patent [19]

Kidani et al.

[11] Patent Number: 4,477,387

[45] Date of Patent: Oct. 16, 1984

[54] PLATINUM(II) COMPLEXES

[75] Inventors: Yoshinori Kidani; Masahide Noji, both of Nagoya, Japan

[73] Assignee: Otsuka Chemical Co., Ltd., Osaka, Japan

[21] Appl. No.: 355,742

[22] PCT Filed: Mar. 4, 1981

[86] PCT No.: PCT/JP81/00154

§ 371 Date: Mar. 2, 1982

§ 102(e) Date: Mar. 2, 1982

[87] PCT Pub. No.: WO82/00145

PCT Pub. Date: Jan. 21, 1982

[30] Foreign Application Priority Data

Jul. 5, 1980 [JP] Japan ............................. 55-92066

[51] Int. Cl.³ ............................................. C07F 15/00
[52] U.S. Cl. ................................. 260/429 R; 424/287
[58] Field of Search ..................... 260/429 R; 424/287

[56] References Cited

U.S. PATENT DOCUMENTS

| | | | |
|---|---|---|---|
| 4,115,418 | 9/1978 | Gale et al. | 260/429 R |
| 4,140,707 | 2/1979 | Cleare et al. | 260/429 R |
| 4,169,846 | 10/1979 | Kidani et al. | 260/429 R |
| 4,200,583 | 4/1980 | Kidani et al. | 260/429 R |
| 4,203,912 | 5/1980 | Hydes et al. | 260/429 R |
| 4,250,189 | 2/1981 | Hydes et al. | 260/429 R |
| 4,255,347 | 3/1981 | Kidani et al. | 260/429 R |
| 4,271,085 | 6/1981 | Amundsen et al. | 260/429 R |

FOREIGN PATENT DOCUMENTS 44620  4/1979  Japan.
55-13280  1/1980  Japan.

OTHER PUBLICATIONS

Heilbron et al., Dictionary of Organic Compounds, Oxford Univ. Press, NY, p. 598 (1953).

Primary Examiner—Helen M. S. Sneed
Attorney, Agent, or Firm—Armstrong, Nikaido, Marmelstein & Kubovcik

[57] ABSTRACT

Platinum(II) complexes comprising platinum(II), a diamine, a ligand of D-gluconic acid and an inorganic or organic anion or ligand, and effecting superior antineoplastic activity at a smaller dose.

9 Claims, 3 Drawing Figures

PLATINUM(II) COMPLEXES

DESCRIPTION

Technical Field

The present invention relates to novel platinum(II) complexes and antineoplastic agents containing the same as effective ingredients.

Background Art

It has been found by the studies of Barnett Rosenberg et. al. that a certain kind of platinum(II) complex has an antineoplastic activity in that they bond with a DNA of a neoplasm, particularly malignant neoplasm to prevent the synthesis of its DNA.

However, many platinum(II) complexes in the primary stage do not have enough maximum antineoplastic activities but have quite strong toxicities for humans.

DISCLOSURE OF INVENTION

As a result of extensive and thorough researches, the inventors had found the fact that platinum(II) complexes represented by the general formula:

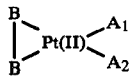

wherein —B—B— is

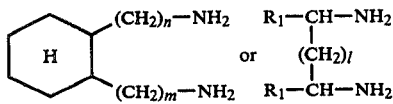

(in which $R_1$ and $R_2$ are the same or different and each is hydrogen, an alkyl group or an aryl group, and n, m and l are 0 or is an integer of from 1 to 3), at least one of $A_1$ and $A_2$ is

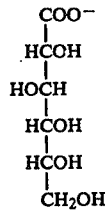

(hereinafter referred to as a ligand of D-gluconic acid) and the other is the ligand of D-gluconic acid, $Cl^-$, $Br^-$, $I^-$, $F^-$, $XCH_2COO^-$ (in which X is a halogen atom), $NO_3^-$, $SO_4^{--}$, $H_2PO_4^-$ or $H_2O$ or, when taken together, $A_1$ and $A_2$ may form a ring together with Pt(II), in the latter case —$A_1$—$A_2$— being the ligand of D-gluconic acid have antineoplastic activities, and then completed the present invention.

In comparison with the known platinum(II) complexes which are of a ligand of glucuronic acid as $A_1$ and/or $A_2$ in the above-mentioned general formula, the platinum(II) complexes of the invention have superior medical effects that the present complexes show their maximum antineoplastic activities in the dose of about one-fourth of the known complexes and are effective as antineoplastics in a wide range of doses.

The —B—B— in the platinum(II) complexes of the invention is roughly classified into the following two diamines.

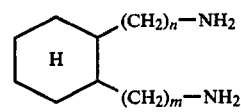

wherein n and m are as defined above.

Examples of such type are, for instance, 1,2-diaminocyclohexane (hereinafter referred to as dach), 1-amino-2-aminomethylcyclohexane (hereinafter referred to as aamch), and the like.

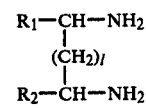

wherein $R_1$, $R_2$ and l are as defined above.

Examples of such type are, for instance, ethylenediamine, trimethylenediamine, 1,2-diphenylethylenediamine (hereinafter referred to as stien), 1-phenylethylenediamine (hereinafter referred to as C-phenen), and the like.

There are isomers of dach and aamch in the type(A) and stien and C-phenen in the type(B), and among them cis-form, trans-d-form and trans-l-form of dach; cis-d-form, cis-l-form, trans-d-form and trans-l-form of aamch; trans-d-form, trans-l-form and meso-form of stien; and d-form and l-form of C-phenen have preferable antineoplastic activities.

$A_1$ and $A_2$ are groups which are liberated when the platinum(II) complex bonds with DNA, and are roughly classified into the following two groups.

(C) At least one of $A_1$ and $A_2$ is the ligand of D-gluconic acid, and the other is $Cl^-$, $Br^-$, $I^-$, $F^-$, $XCH_2COO^-$ (in which X is as defined above), $NO_3^-$, $SO_4^{--}$, $H_2PO_4^-$ or $H_2O$.

(D) $A_1$ and $A_2$, when taken together, form a ring together with Pt(II) and —$A_1$—$A_2$— is the ligand of D-gluconic acid.

Examples of the platinum(II) complexes are, for instance, shown in Table 1. In Table 1 D-gluco represents the ligand of D-gluconic acid.

TABLE 1

| Complex No. | Platinum (II) complexes |
|---|---|
| 1 | Pt(D-gluco)H₂O(cis-dach).NO₃ |
| 2 | Pt(D-gluco)H₂O(trans-d-dach).NO₃ |
| 3 | Pt(D-gluco)H₂O(trans-l-dach).NO₃ |
| 4 | Pt(D-gluco)H₂O(cis-dach).½ SO₄ |
| 5 | Pt(D-gluco)H₂O(trans-d-dach).½ SO₄ |
| 6 | Pt(D-gluco)H₂O(trans-l-dach).½ SO₄ |
| 7 | Pt(D-gluco)₂(cis-dach) |
| 8 | Pt(D-gluco)₂(trans-d-dach) |
| 9 | Pt(D-gluco)₂(trans-l-dach) |
| 10 | Pt(D-gluco)H₂O(cis-d-aamch).NO₃ |
| 11 | Pt(D-gluco)H₂O(cis-l-aamch).NO₃ |
| 12 | Pt(D-gluco)H₂O(trans-d-aamch).NO₃ |
| 13 | Pt(D-gluco)H₂O(trans-l-aamch).NO₃ |
| 14 | Pt(D-gluco)H₂O(cis-d-aamch).½ SO₄ |
| 15 | Pt(D-gluco)H₂O(cis-l-aamch).½ SO₄ |
| 16 | Pt(D-gluco)H₂O(trans-d-aamch).½ SO₄ |
| 17 | Pt(D-gluco)H₂O(trans-l-aamch).½ SO₄ |
| 18 | Pt(D-gluco)H₂O(trans-d-stien).NO₃ |
| 19 | Pt(D-gluco)H₂O(trans-l-stien).NO₃ |
| 20 | Pt(D-gluco)H₂O(meso-stien).NO₃ |

TABLE 1-continued

| Complex No. | Platinum (II) complexes |
|---|---|
| 21 | Pt(D-gluco)H$_2$O(trans-d-stien).½ SO$_4$ |
| 22 | Pt(D-gluco)H$_2$O(trans-l-stien).½ SO$_4$ |
| 23 | Pt(D-gluco)H$_2$O(meso-stien).½ SO$_4$ |
| 24 | Pt(D-gluco)$_2$(trans-d-stien) |
| 25 | Pt(D-gluco)$_2$(trans-l-stien) |
| 26 | Pt(D-gluco)$_2$(meso-stien) |
| 27 | Pt(D-gluco)H$_2$O(d-C—phenen).Cl |
| 28 | Pt(D-gluco)H$_2$O(l-C—phenen).Cl |

The platinum(II) complexes can be prepared by applying the known processes, e.g. the process described in Journal of Pharmaceutical Sciences, Vol.65, 315–328(1976).

That is, (1) by reacting K$_2$PtX$_4$(X is as defined above) with the above-mentioned diamines (—B—B—, hereinafter referred to as B$_2$), B$_2$Pt(II)X$_2$ can be obtained. Substitution of the halogen atom can be effected by reacting a halide of potassium or sodium with B$_2$Pt(II)X$_2$.

(2) B$_2$Pt(II)(NO$_3$)$_2$ and B$_2$Pt(II)(SO$_4$) can be obtained by suspending B$_2$Pt(II)X$_2$ obtained in (1) in water, adding silver nitrate or silver sulfate thereto, respectively, and reacting with shielding the light.

(3) D-gluconates and monobromoacetates of B$_2$Pt(II) can be obtained by dissolving B$_2$Pt(II)(NO$_3$)$_2$ in water with heating and reacting sodium D-gluconate and monobromoacetic acid therewith respectively. In case of the reaction with D-gluconic acid, a ring is formed with heating These reactions are conducted in water with heating or with shielding the light, if necessary. After 3 to 48 hours the reactions re normally completed to give a white or yellow precipitate, and then the complexes of invention can be obtained in the form of crystal or powder.

As the diamines used in the above-mentioned process(1), those of the above-mentioned types(A) and (B) can be employed. For example, when diamines of trans-d-form are used as the diamines, B$_2$ in the desired platinum(II) complexes is trans-d-form.

For preparing each isomer of dach, for example, a methanol solution of a commercially available dach is reacted with NiCl$_2$.6H$_2$O to precipitate Ni(cis-dach)$_2$Cl$_2$ and to leave Ni(trans-dach)$_2$Cl$_2$ in the filtrate. Ni(cis-dach)$_2$Cl$_2$ is dissolved in sulfuric acid, the resulting solution was concentrated, cis-dach.H$_2$SO$_4$ is obtained from the concentrate in ethanol and after adding a large excess of sodium hydroxide thereto cis-dach is obtained by extraction with chloroform. Trans-dach.2HCl is precipitated by adding hydrochloric acid to Ni(trans-dach)$_2$Cl$_2$ in the filtrate, concentrating under reduced pressure and adding ethanol or acetone thereto. Trans-dach is obtained by treating the resulting trans-dach 2HCl in the same manner as in cis-dach.

In resolution of trans-dach into d-form and l-form, trans-l-dach is obtained by reacting trans-dach with d-tartaric acid to give (trans-l-dachH$_2$)(d-tartaric acid), dissolving it in a small amount of water, adding KOH thereto, extracting with ether and distilling off ether. For obtaining trans-d-dach, l-tartaric acid may be employed instead of d-tartaric acid.

Resolution from a racemic form of aamch into d-form and l-form is conducted by reacting dibenzoyl-d-tartaric acid and dibenzoyl-l-tartaric acid therewith respectively.

Meso-form of stien can be obtained by acetylating amarin and hydrolyzing. Trans-d-form and trans-l-form can be resolved by acetylating isoamarin, refluxing in the presence of glacial acetic acid and hydrobromic acid to give trans-d,l-stiens and reacting them with l-tartaric acid and d-tartaric acid.

The present invention also relates to antineoplastic agents containing the platinum(II) complexes represented by the above-mentioned general formula as active ingredients.

The antineoplastic agents attack the DNA of neoplasm cells to exhibit very excellent antineoplastic activity as well as to lower the nephrapathy which is a problem in cis-[Pt(NH$_3$)$_2$Cl$_2$].

The dose of the antineoplastic agent varies with the condition of a patient and the kind of neoplasm, and the complexes of the invention which are the active ingredients may be administered at 3 to 500 mg./kg., preferably 3 to 100 mg./kg. per day.

Preparation forms of the agents are, for example, injections, suppositories, topical administrations, and the like. As injections, included are aqueous or oily suspensions or solutions, powder fillers or freeze-drying powders which are dissolved when used, and they can be prepared by a conventional manner. They are preferably administrated hypodermatically or intravenously. There is no problem for preparation of injections because the platinum(II) complexes of the invention are soluble in water quite easily.

The suppositories can be prepared with the conventional bases. As the bases there are employed, for instance, polyethyleneglycol, lanolin, cacao butter, a fatty acid triglyceride, and the like.

As the topical administrations, included are, for example, ointments, creams, and the like, and they can be prepared with the conventional bases. As the bases there are listed up, for instance, liquid paraffin, acetyl alcohol, white vaseline, squalane, lanolin, cholesterol, glycerol, fatty acid esters, and the like.

The antineoplastic agents can also be used as oral administrations. As the oral administrations, included are, for instance, tablets, capsules, granules, fine granules, powders, syrups, and the like. The granules, fine granules and powders can be also used in a form of individual doses wrapped in chartulatae. Excipients used for their preparations are, for example, milk sugar, sucrose, starch, talc, magnesium stearate, crystalline cellulose, methylcellulose, carboxymethylcellulose, glycerol, sodium alginate, gum arabic, and the like.

BEST MODE FOR CARRYING OUT THE INVENTION

Figure 1:
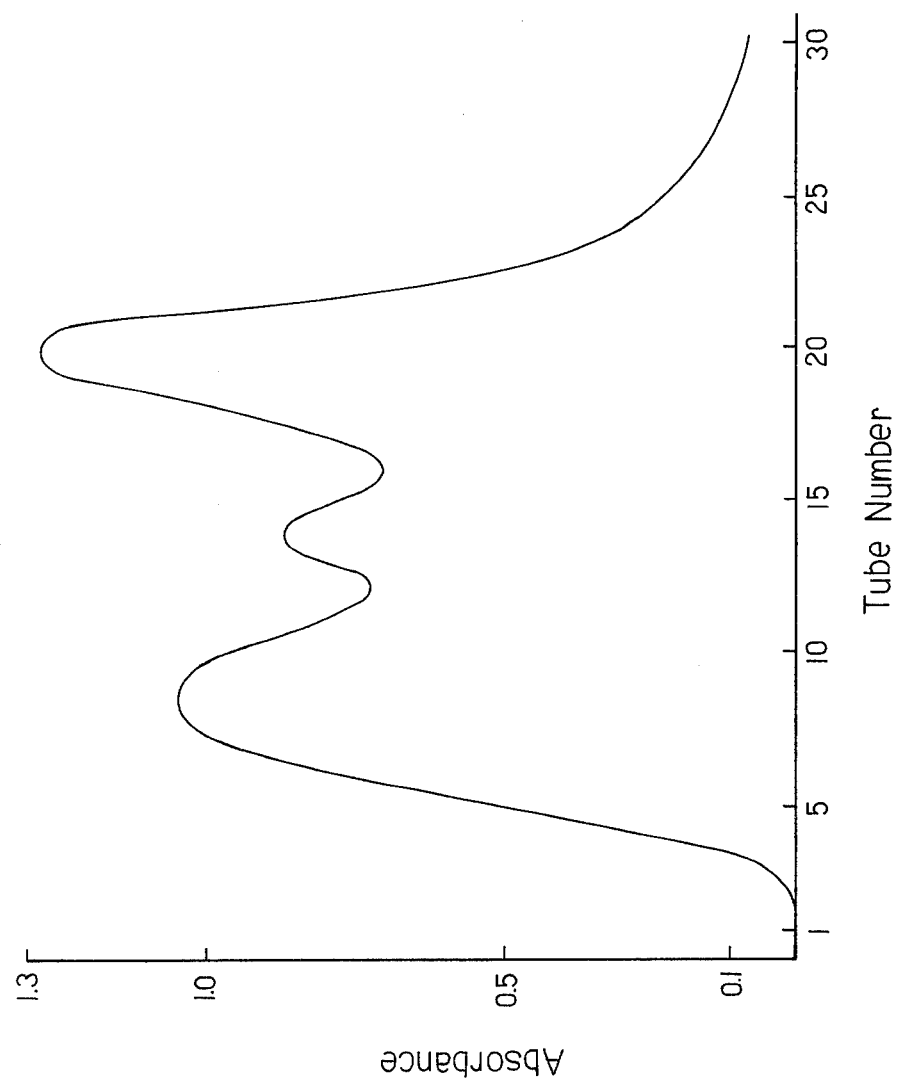
FIG. 1 shows the UV spectrum chart of the crude product in Example 1.

The present invention is described in detail with the following Reference Examples, Examples, Test Examples and Preparation Examples.

REFERENCE EXAMPLE 1

Resolution of dach (Preparation of (trans-l-dachH$_2$)(d-tartaric acid))

To 160 ml. of a methanol solution of 25 g. (0.22 mole) of dach manufactured by Tokyo Kasei Kogyo Kabushiki Kaisha was added 440 ml. of a methanol solution dissolving 26 g.(0.11 mole) of $NiCl_2.6H_2O$ and the reaction was conducted for two hours at room temperature with stiring. The resulting yellow precipitate was collected by filtration, washed well with methanol and air-dried to give 7.9 g. of $Ni(cis\text{-}dach)_2Cl_2$. To the filtrate 35 ml. of 6N-HCl was added, pH of the mixture was adjusted by 15%-NaOH to 4.2 to 4.5. The resulting bluish violet precipitate was collected by filtration, washed well with water and air-dried to give 18.1 g. of $Ni(trans\text{-}dach)_2(H_2O)_2.Cl_2$.

The above-mentioned yellow $Ni(cis\text{-}dach)_2Cl_2$ was dissolved in 15 ml. of $6N\text{-}H_2SO_4$, the resultant was concentrated under reduced pressure and added 80 ml. of ethanol thereto to give a colorless precipitate. The precipitate was collected by filtration, washed well with ethanol and air-dried to obtain 8.4 g. of cis-dach.$H_2SO_4$. After dissolving it in a small amount of water, cis-dach was liberated by adding a large excess of 25%-NaOH and the liberated cis-dach was extracted with chloroform. The chloroform solution was dried with $K_2CO_3$ and distilled under reduced pressure to give 3.2 g. of cis-dach in the form of colorless liquid.

$R_f=0.25$ b.p.: 39° to 41° C.

To the above-mentioned violet $Ni(trans\text{-}dach)_2(H_2O)_2Cl_2$ was added 30 ml. of 6N-HCl and 150 ml. of acetone to give a colorless precipitate. The precipitate was collected by filtration, washed well with an ethanol-acetone and air-dried to give 14.6 g. of trans-dach.2HCl. fifty three grams of trans-dach was obtained in the form of colorless liquid by the liberation in the same manner as in the cis-form.

$R_f=0.45$ b.p.: 41° to 42° C./2 mm.Hg $R_f$ value was measured by TLC using a silica gel and a mixture of ethanol:tetrahydrofuran:diethylamine:-water=6:3:3:1 as a developer.

The resolution of trans-form into d-form and l-form was conducted by adding 10 ml. of water to 5.3 g. of trans-dach, dissolving with heating at 90° C., adding 3.3 g. of d-tartaric acid and 20 ml. of glacial acetic acid thereto little by little, cooling at 0° C. for about 12 hours and recrystallizing the crude (trans-l-dachH$_2$)(d-tartaric acid) from water to give 245 g. of crystal (Yield 50%).

Specific rotation: $[\alpha]_D^\circ = +122°$ C.(1% $H_2O$)

Elementary analysis: Found(%): C45.45, H7.63, N10.60. Calculated(%): C45.49, H7.74, N10.74.

Preparation of trans-l-dach

By dissolving (trans-l-dachH$_2$)(d-tartaric acid) to a small amount of water and adding 1.5 g. of KOH, trans-l-dach was liberated therefrom and extracted with ether rapidly. After distilling off ether, 23 g. of trans-l-dach was obtained by distilling under reduced pressure in nitrogen atmosphere.

Preparation of trans-d-dach.2HCl

Twenty one grams of trans-d-dach.2HCl was obtained by reacting l-tartaric acid with the remaining mother liquor free of trans-l-dach and treating in the same procedure as in the trans-l-dach.

b.p.: 41° to 42° C./2 mm.Hg

Elementary analysis: Found(%): C38.50, H8.55, N17.48. Calculated(%): C38.52, H8.62, N14.97.

EXAMPLE 1

Preparation(I) of Pt(D-gluco)H$_2$O(dach).NO$_3$ and Pt(D-gluco)$_2$(dach)

In 100 ml. of water 433 mg. (1 m.mole) of Pt(cis-dach).(NO$_3$)$_2$(molecular weight 433) was dissolved with warming on a water bath.

An aqueous solution obtained by dissolving 220 mg.(1 m.mole) of sodium D-gluconate in 10 to 20 ml. of water was mixed with aqueous solution of the above-mentioned Pt(cis-dach).(NO$_3$)$_2$ and the reaction was conducted.

The reaction was conducted by allowing to stand at 10° to 20° C. for 3 to 4 weeks.

Treatment 1

After the obtained reaction mixture was filtered, the filtrate was concentrated to dryness with a flash evaporator, and further concentrated to dryness twice by adding anhydrous ethanol and then anhydrous acetone in order to remove water completely from the concentrated dry material. Subsequently, to the dry material anhydrous ethanol was added carefully because the dry material is very hygroscopic, and the dry material was collected on a glass filter by filtration to give a cololess or light yellow powder. After washing the powder with an alcohol and then acetone, 650 mg. of the product was obtained.

Treatment 2

In about 50 ml. of water 650 mg. of the powder obtained in Treatment 1 was dissolved and the resulting solution was eluted by column chromatography with Sephadex G-10(commercial name, manufactured by Pharmacia A. B.) using demineralized water. The eluates were collected every 3 to 5 ml. by a fraction collector and the elution carve was drawn up by measuring a UV absorbance at 250 nm. of each fraction.

There were observed three peaks(a), (b) and (c) as in FIG. 1.

Treatment 3

Figure 2:
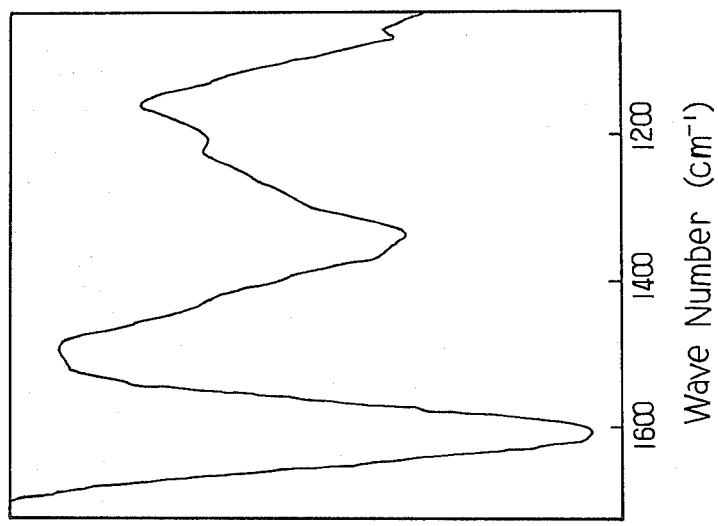

The fractions of the peak(b) were collected, and the collected fractions were concentrated to dryness at as low temperatures as possible of not more than 50° C. in the same manner as in Treatment 1 to give a colorless or slightly yellow dry material. To the obtained dry material anhydrous methanol was added and 80 to 100 mg. of Pt(D-gluco)H$_2$O(cis-dach)NO$_3$ was collected by filtration (Yield 13 to 18%). The characteristic part of the chart of the complex analyzed by IR spectrum analysis is shown in FIG. 2.

Elementary analysis: (molecular weight 566.4): Found(%): C25.45, H4.79, N6.89. Calculated(%): C24.66, H4.66, N7.19.

The fractions of the peaks(a) and (c) obtained in Treatment 2 were treated in the same manner as in Treatment 3 to give 170 mg. of brown Pt(D-gluco)$_2$(cis-dach) (Yield 30%) and 100 mg. of the starting Pt(cis-dach)(NO$_3$)$_2$(Yield 20%), respectively.

Figure 3:
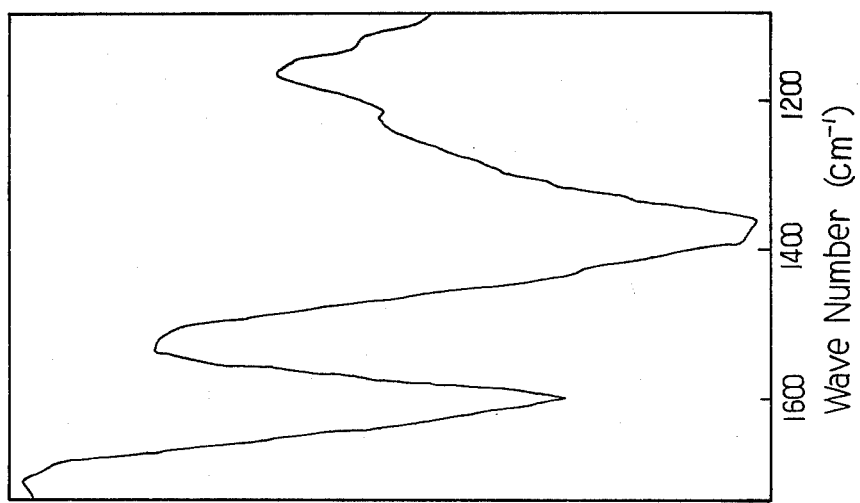
FIGS. 2 and 3 show the characteristic parts of the respective IR spectrum charts of Pt(D-gluco) H$_2$O(cis-dach).NO$_3$ and Pt(D-gluco)$_2$(cis-dach).

The results of the analysis of Pt(D-gluco)$_2$ (cis-dach) are shown below. Besides, the characteristic part of the chart of the complex analyzed by IR spectrum analysis is shown in FIG. 3.

Elementary analysis: (Pt(D-gluco)$_2$(cis-dach)2H$_2$O, molecular weight 713.5): Found(%): C29.69, H5.72, N3.80. Calculated(%): C29.47, H5.50, N3.82.

In order to improve the yeild of Pt(D-gluco)₂(cis-dach), the reaction was conducted with the starting material in which the molar ratio of Pt(NO₃)₂(cis-dach) to sodium D-gluconate was 1:2 and Treatments 1 to 3 were effected on the reaction mixture. In such case, the yeild of Pt(D-gluco)₂(cis-dach) was 50 to 60%.

Except employing Pt(NO₃)₂(trans-d-dach) and Pt(NO₃)₂(trans-l-dach) instead of Pt(NO₃)₂(cis-dach), the same procedures as in Pt(NO₃)₂(cis-dach) were effected to give Pt(D-gluco)₂H₂O(trans-d-dach)NO₃ and Pt(D-gluco)₂(trans-d-dach), and Pt(D-gluco)H₂O(trans-l-dach).NO₃ and Pt(D-gluco)₂(trans-l-dach), respectively. The results of the analysis of them are as follows:

(Pt(D-gluco)H₂O(trans-d-dach).NO₃)
Elementary analysis: (molecular weight 566.4):
Found(%): C24.86, H4.73, N7.00. Calculated(%): C24.66, H4.66, N7.19.

(Pt(D-gluco)₂(trans-d-dach).H₂O)
Elementary analysis: (molecular weight 695.5):
Found(%): C29.42, H5.37, N4.05. Calculated(%): C30.22, H5.35, N3.92.

(Pt(D-gluco)H₂0(trans-l-dach).NO₃)
Elementary analysis: (molecular weight 566.4):
Found(%): C24.71, H4.72, N6.98. Calculated(%): C24.66, H4.66, N7.19.

(Pt(D-gluco)₂(trans-l-dach).3H₂O)
Elementary analysis: (molecular weight 731.5):
Found(%): C28.77, H5.63, N3.73. Calculated(%): C28.63, H5.38, N3.37.

Besides, a dry powder of the reaction product can be also obtained by filtering the reaction mixture and then freeze-drying instead of the above-mentioned Treatment 1.

EXAMPLE 2

Preparation(II) of Pt(D-gluco)H₂O(dach).NO₃ and Pt(D-gluco)₂(dach)

Pt(D-gluco)H₂O(cis-dach).NO₃ and Pt(D-gluco)₂(cis-dach) were obtained by treating the starting materials, i.e. an aqueous solution of sodium D-gluconate and an aqueous solution of Pt(NO₃)₂(cis-dach) in the same manner as in Example 1 except reacting the starting materials with mixing, allowing to stand at about 50° C. for a day and night, and then warming at 50° to 60° C. for 6 to 8 hours on a water bath instead of reacting them by allowing to stand for 3 to 4 weeks.

When 1:1 and 2:1 were employed as the molar ratios of sodium D-gluconate to Pt(NO₃)₂(cis-dach), the respective yeilds of Pt(D-gluco)₂(cis-dach) were not less than 30% and 60 to 70%.

In case of employing trans-d-dach and trans-l-dach instead of cis-dach, the corresponding platinum(II) complexes were obtained.

As a result of analyzing those platinum(II) complexes, it was identified that elementary analysis, melting points and specific rotations thereof were the same as those of the complexes obtained in Example 1.

REFERENCE EXAMPLE 2

Resolution of trans or cis-d,l-aamch

In 100 ml. of water 17.7 g. of trans-d,l-aamch and 51.8 g. of dibenzoyl-d-tartaric acid were suspended and stirred, and the precipitated solid material was washed with ethanol several times, and then (trans-l-aamch)(dibenzoyl-d-tartaric acid) was obtained by repeatedly recrystallizing from water-ethanol (1:1 by volume). Specific roation [α]_D²³ of it was −97.78°.

The obtained (trans-l-aamch)(dibenzoyl-d-tartaric acid) was added to water. A concentrated hydrochloric acid was added thereto and dibenzoyl-d-tartaric acid which was liberated was filtered out. After neutralizing the obtained mother liquor by adding caustic soda, the liberated trans-l-aamch was extracted with ether and trans-l-aamch was obtained by distilling off ether.

Trans-d-aamch was obtained by employing dibenzoyl-l-tartaric acid in the same manner as the above. Cis-d,l-aamch was resolved into cis-d-aamch and cis-l-aamch in the same manner as in trans-form except employing cis-d,l-aamch.

EXAMPLE 3

Preparation of Pt(D-gluco)H₂O(aamch).NO₃

Sixty mg. of Pt(D-gluco)H₂O(cis-d-aamch).NO₃ was obtained by reacting and treating in the same manner as in Treatments 1 to 3 in Example 1 except employing 477 mg.(1 m.mole) of Pt(cis-d-aamch)(NO₃)₂ and 218 mg.(1 m.mole) of sodium D-gluconate (Yield 12%).

Pt(D-gluco)H₂O(cis-l-aamch).NO₃, Pt(D-gluco)H₂O(trans-d-aamch).NO₃ and Pt(D-gluco)H₂O(trans-l-aamch)NO₃ were obtained in the same manner as the above by employing Pt(cis-l-aamch)(NO₃)₂, Pt(trans-d-aamch)(NO₃)₂ and Pt(trans-l-aamch)(NO₃)₂ respectively, as the starting materials instead of Pt(cis-d-aamch)(NO₃)₂.

REFERENCE EXAMPLE 3

Resolution of stien (1) Preparation of meso-stien

Two hundred and ninety eight mg. of amarin was acetylated with 60 mg. of acetic acid in the presence of hydrochloric acid to give 350 mg. of N-benzoyl-N'-acetyl-stilbenediamine. To the diamine 50% of sulfuric acid was added, and the reaction was conducted for 3 hours at room temperature and the resulting reaction mixture was subjected to recrystallization from hot water to give 175 mg. of meso-stien (Yield 50%).

(2) Preparation of trans-d,l-stien

After adding 298 mg. of amarin to a mixture of diethyleneglycol, water and NaOH, the reaction was conducted at 155° C. for 45 minutes to give 290 mg. of isoamarin. Subsequently, the isoamarin was acetylated with 60 mg. of acetic acid in the presence of hydrochloric acid to give 350 mg. of N-benzoyl-N'-acetylstilbenediamine, and the diamine was subjected to reflux for 24 hours in the presence of glacial acetic acid and hydrobromic acid, and the resulting reaction mixture was extracted with ether to give 157 mg. of trans-d,l-stien (Yield 45%).

(3) Resolution of trans-d,l-stien

One hundred and fifty seven mg. of trans-d,l-stien obtained in (2) was optically resolved by reacting with d- and l-tartaric acid to give trans-l-stien and trans-d-stien respectively. The specific rotations ([α]_D, 0.1% ethanol) of trans-d-stien and trans-l-stien were +80.0° and −78.0° respectively.

EXAMPLE 4

Prearation of Pt(D-gluco)H₂O(stien).NO₃

Pt(D-gluco)H₂O(trans-d-stien).NO₃ was obtained in the same manner as in Example 3 except employing Pt(NO₃)₂(trans-d-stien) instead of Pt(NO₃)₂(dach) (Yield 10%).

Pt(D-gluco)H₂O(trans-l-stien).NO₃ was obtained by employing Pt(NO₃)₂(trans-l-stien) instead of Pt(NO₃)₂(trans-d-stien).

EXAMPLE 5

Preparation of Pt(D-gluco)H₂O(stien).½SO₄

Pt(D-gluco)H₂O(trans-d-stien).½SO₄ was obtained in the same manner as in Example 4 except employing 1 m.mole of Pt(SO₄)(trans-d-stien) instead of Pt(NO₃)₂(trans-d-stien) (Yield 13%).

Pt(D-gluco)H₂O(trans-l-stien).½SO₄ was obtained by employing Pt(SO₄)(trans-l-stien) instead of Pt(SO₄)(trans-d-stien).

EXAMPLE 6

Preparation of Pt(D-gluco)₂(stien)

Two isomers, Pt(D-gluco)₂(trans-d-stien) and Pt(D-gluco)₂(trans-l-stien) were obtained in the same manner as in Example 5 except employing 2 m.moles (436 mg.) of sodium D-gluconate (Yield 40%).

TEST EXAMPLES

Acute toxity test

Acute toxity (LD₅₀) test was conducted with ddN mice (male). As the compounds to be tested the platinum(II) complexes shown in Table 2 were employed and the suspensions of each compounds in 0.3% CMC were intraperitoneally administrated at 0.5 ml. per mouse.

TABLE 2

| No. of Platinum (II) complexes | LD₅₀ (mg./kg.) |
| --- | --- |
| 1 | 21.2 |
| 3 | 15.6 |
| 5 | 32.3 |
| 7 | 41.6 |
| 10 | 22.4 |
| 12 | 31.5 |
| 14 | 15.8 |
| 18 | 27.6 |

Antineoplastic activity

As the animals for the test, 10 male CDF mice (average body weight 20 g.) were employed with respect to every platinum(II) complex. L 1210 (the number of transplanted cells was 10⁵ per mouse) was administrated intraperitoneally to the mice and the platinum(II) complexes of the invention in Table 3 were administrated intraperitoneally at the doses shown in the same Table on the day when L 1210 was administrated, on the fifth day and nineth day.

The antineoplastic activities were evaluated by the percentage of elongation of the average of survival period (T/C%)(average of survival days in the platinum(II) complex administrated group) and the platinum(II) complexes which had not less than 125% activities were regarded as effective.

TABLE 3

| No. of platinum (II) complex | T/C (%) dose (mg./kg.) | | | |
| --- | --- | --- | --- | --- |
|  | 50 | 25 | 12.5 | 6.25 |
| 1 | — | 181 | 181 | — |
| 2 | — | 244 | 230 | 150 |
| 3 | — | 304 | 277 | 290 |
| 7 | — | 212 | 166 | — |
| 8 | — | 148 | 132 | 119 |
| 9 | — | 304 | 166 | 139 |
| 10 | — | 225 | 262 | 237 |
| 11 | — | 250 | 300 | 191 |
| 12 | — | 191 | 164 | 135 |
| 13 | — | 256 | 193 | 170 |
| 18 | 101 | 111 | 104 | — |
| 19 | 219 | 161 | 150 | — |
| 21 | 130 | 115 | — | — |
| 22 | 215 | 169 | — | — |
| 26 | 261 | 176 | 181 | — |

| Prescription Example | |
| --- | --- |
| [Capsule] | (mg.) |
| Pt(D-gluco)H₂O(cis-dach).NO₃ | 21.5 |
| Milk sugar | 50 |
| Potato starch | 50 |
| Crystalline cellulose | 109 |
| Magnesium stearate | 1 |
| [Granule] | (mg.) |
| Pt-(D-gluco)H₂O(trans-d-dach).½ SO₄ | 32.1 |
| Milk sugar | 550 |
| Corn starch | 330 |
| Hydroxypropylcellulose | 20 |
| [Suppository] | (mg.) |
| Pt(D-gluco)H₂O(cis-d-aamch).NO₃ | 30.5 |
| Witepsol W-35 (Commercial name, manufactured by Dynamite Nobel AG) | 500 |
| [Ointment] | (g.) |
| Pt(D-gluco)H₂O(trans-d-stien).NO₃ | 25.5 |
| White vaseline | 23.0 |
| Stearyl alcohol | 22.0 |
| Propyleneglycol | 12.0 |
| Sodium laurylsulfate | 1.5 |
| Ethyl p-hydroxybenzoate | 0.025 |
| Propyl p-hydroxybenzoate | 0.015 |
| Purified water | optimum |

We claim:

1. A platinum(II) complex represented by the general formula:

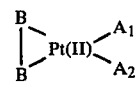

wherein —B—B— is

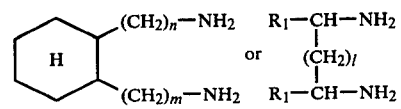

(in which R₁ and R₂ are the same or different and each is hydrogen, an alkyl group or an aryl group, and n, m and l are 0 or is an integer of from 1 to 3), at least one of A₁ and A₂ is

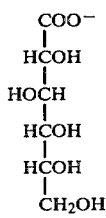

and the other is

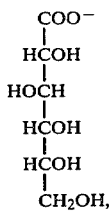

$Cl^-$, $Br^-$, $I^-$, $F^-$, $XCH_2COO^-$ (in which X is a halogen atom), $NO_3^-$, $SO_4^{--}$, $H_2PO_4^-$ or $H_2O$ or, when taken together, $A_1$ and $A_2$ may form a ring together with Pt(II), in the latter case $-A_1-A_2-$ being

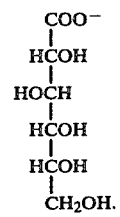

2. The platinum(II) complex of claim 1, wherein at least on of $A_1$ and $A_2$ in said general formula is

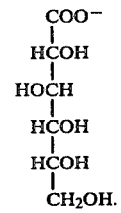

3. The platinum(II) complex of claim 1 or 2, $-B-B-$ is 1,2-diaminocyclohexane.

4. The platinum(II) complex of claim 3, wherein said 1,2-diaminocyclohexane is cis-form, trans-d-form or trans-l-form.

5. The platinum(II) complex of claim 1 or 2, wherein $-B-B-$ in said general formula is 1-amino-2-aminomethylcyclohexane.

6. The platinum(II) complex of claim 5, wherein said 1-amino-2-aminomethylcyclohexane is cis-d-form, cis-l-form, trans-d-form or trans-l-form.

7. The platinum(II) complex of claim 1 or 2, wherein $-B-B-$ in said general formula is 1,2-diphenylethylenediamine.

8. The platinum(II) complex of claim 7, wherein said 1,2-diphenylethylenediamine is meso-form, trans-d-form or trans-l-form.

9. The platinum(II) complex of claim 1 or 2, wherein $-B-B-$ in said general formula is 1-phenylethylenediamine.

* * * * *